US00PP28229P3

(12) United States Plant Patent
Olesen

(10) Patent No.: US PP28,229 P3
(45) Date of Patent: Aug. 1, 2017

(54) COMPACT FLORIBUNDA ROSE PLANT NAMED 'POULCAS049'

(50) Latin Name: ***Rosa* hybrid**
Varietal Denomination: Poulcas049

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DE)

( * ) Notice: Subject to any disclaimer, the term of this patent is extended or adjusted under 35 U.S.C. 154(b) by 0 days.

(21) Appl. No.: 14/756,272

(22) Filed: Aug. 20, 2015

(65) Prior Publication Data

US 2017/0055400 P1 Feb. 23, 2017

(51) Int. Cl.
*A01H 5/02* (2006.01)

(52) U.S. Cl.
USPC ..... Plt./150

(58) Field of Classification Search
USPC ..... Plt./150
See application file for complete search history.

(56) References Cited

PUBLICATIONS

Poulsen Roser A/S "Castle-Perfection by Poulsen" Oct. 2012 (1 page).*

* cited by examiner

*Primary Examiner* — Susan McCormick Ewoldt

(57) ABSTRACT

A new garden rose plant of the Compact Floribunda class which has abundant, orange red flowers and attractive foliage. This new and distinct variety has shown to be uniform and stable in the resulting generations from asexual propagation.

2 Drawing Sheets

Botanical designation: *Rosa* hybrid.
Variety denomination: 'Poulcas049'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2008 and the resulting seeds were planted in a controlled environment in Fredensborg, Denmark. The new variety, named 'Poulcas049', originated as a single seedling from the stated cross.

The new variety may be distinguished from its male pollen parent and female seed parent primarily by the following characteristics. The male pollen parent plant has light pink to apricot colored flowers while the new variety has orange red flowers. The female seed parent has medium pink flowers while the new variety has orange red flowers.

The objective of the hybridization of this rose variety was to create a new and distinct variety for garden use with unique qualities, such as:

1. Uniform and abundant orange red flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulcas049' from all other varieties of which we are aware.

As part of the rose development program, Mogens N. Olesen germinated the seeds from the aforementioned hybridization during winter of 2008 and conducted evaluations on the resulting seedlings in a controlled environment in Fredensborg, Denmark. 'Poulcas049' was selected in the spring of 2009 by the inventor as a single plant from the progeny of the aforementioned hybridization.

Asexual reproduction of 'Poulcas049' by traditional budding and rooted cuttings was first done by Mogens N. Olesen in the nursery in Fredensborg, Denmark in July, 2009. This initial and other subsequent asexual propagations conducted in controlled environments have demonstrated that the characteristics of 'Poulcas049' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulcas049'.

Specifically illustrated in FIG. 1 of the drawings are open flower from various perspectives, detached flower petals revealing reproductive flower parts, and flower bud before and upon opening.

Figure 1:
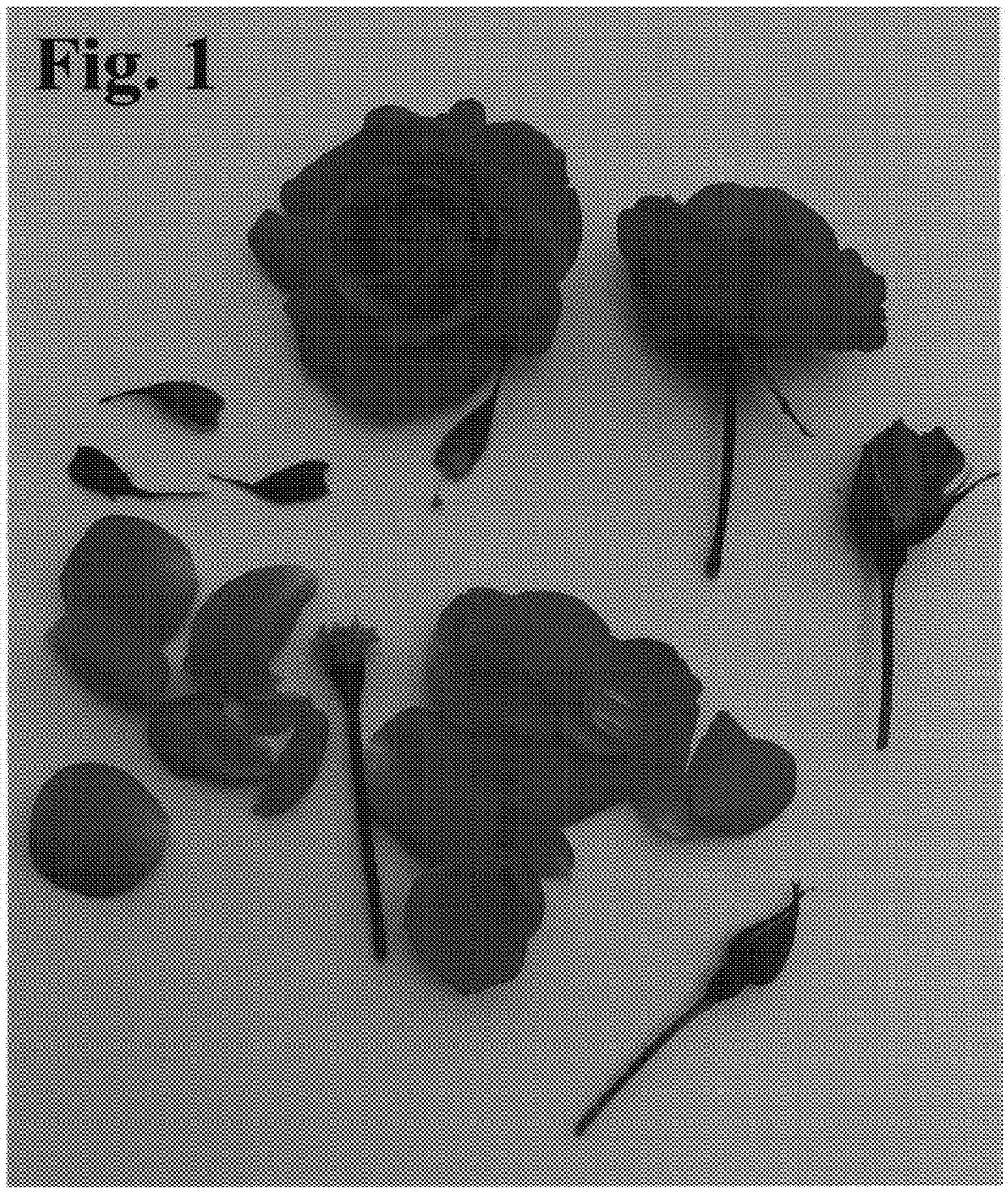
Figure 2:
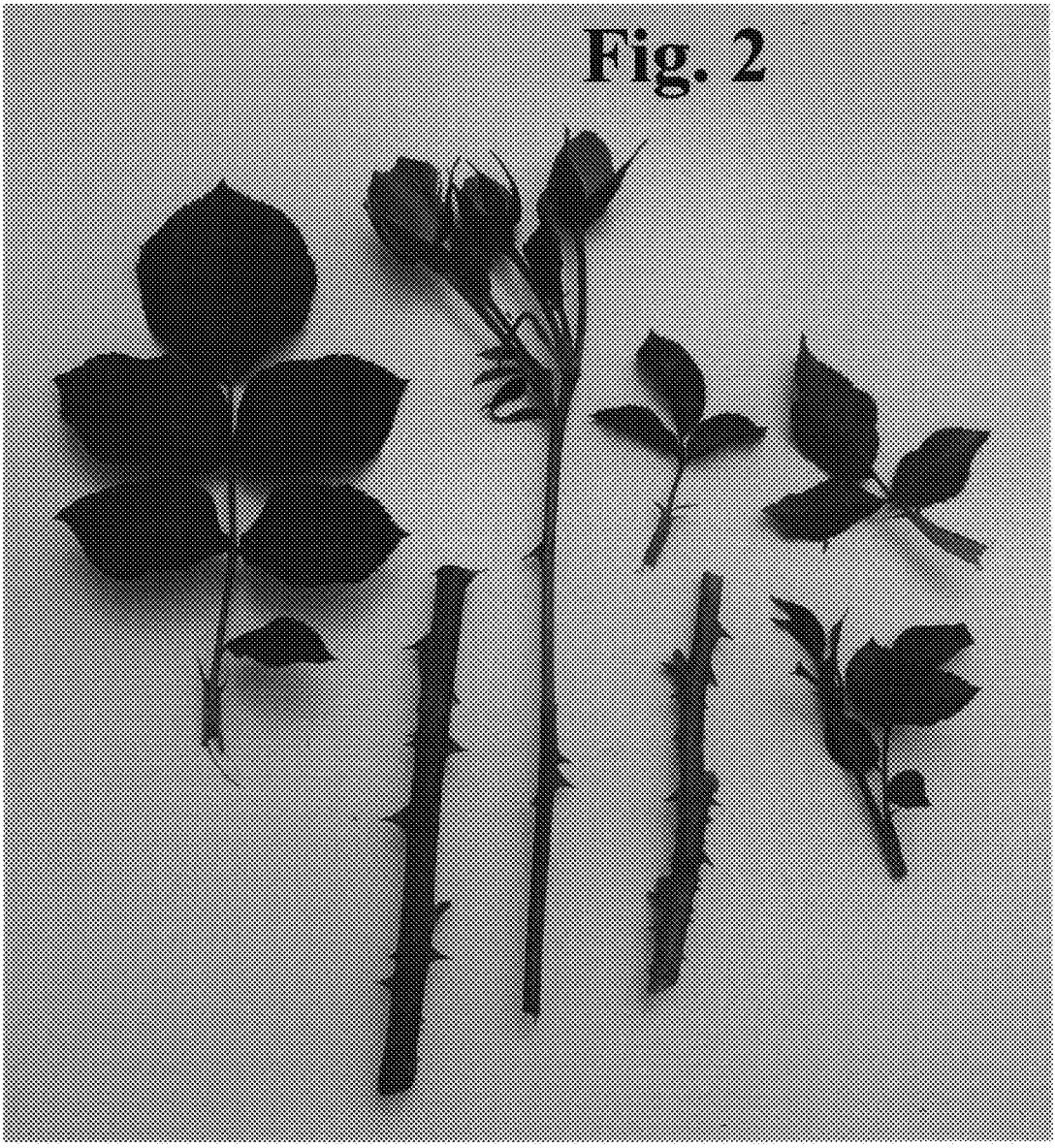

Specifically illustrated in FIG. 2 of the drawings are a cluster of opening flower buds on a branch, stems, juvenile leaves showing dark anthocyanin, and mature leaves. Plants shown are 2 years of age.

DETAILED DESCRIPTION OF THE VARIETY

The following is a description of 'Poulcas049', as observed in its growth in in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulpal024', U.S. Plant Pat. No. 17,031 are compared to 'Poulcas049' in Chart 1.

CHART 1

| | 'Poulcas049' | 'Poulpal024' |
|---|---|---|
| Petal Count | 40 | 55 to 60 |
| Flower Diameter | 70 mm | 60 to 65 mm |
| General Tonality of Flower Color | Red Group 40A | Red Group 41A |

FLOWER AND FLOWER BUD

Blooming habit: Continuous.

Flower bud:

*Size.*—Upon opening, 28 mm in length from base of receptacle to end of bud. Bud diameter is 12 mm.

*Bud form.*—Ovoid.

*Bud color.*—As sepals divide petals are Red Group 40A.

*Sepal inner surface.*—Color: Yellow-Green Group 147D. Surface: Lightly pubescent.

*Sepal outer surface.*—Color: Yellow-Green Group 144A with strong intonations of Greyed-Purple Group 183A. Texture: Smooth.

*Sepal shape.*—Apex: Cirrhose. Base: Flat at union with receptacle.

*Sepal margin.*—Margins have moderate foliaceous appendages on three of the five sepals.

*Sepal size.*—35 mm long, 10 mm wide.

*Receptacle.*—Texture: Smooth. Size: 8 mm in height, 5 mm wide. Color: Yellow-Green Group 144A with strong intonations of Greyed-Purple Group 183A. Shape: Elliptical.

*Pedicel.*—Surface: Rough with small prickles. Length: 35 mm. Diameter: 2 mm on average. Color: Yellow-Green Group 144A with intonations of Greyed-Red Group 180A. Strength: Moderately strong.

*Peduncle.*—Length: 5 to 14 cm. Diameter: About 3 to 5 mm. Color: Yellow-Green Group 145A. Texture: Smooth.

Flower bud development: Flower buds are borne in panicles of 15 to 20 flower buds per stem. Panicles are approximately 20 cm in diameter.

Flower bloom:

*Fragrance.*—Moderate floral scent.

*Duration.*—The blooms have a duration on the plant of approximately 12 days. Petals fall cleanly away from plant after flowers have fully matured.

*Size.*—Flower diameter is 70 mm when open. Flower depth is 25 mm.

*Flower shape.*—Double rosette flower with many slightly overlapping petals of different sizes.

*Shape of flower, side view.*—The upper portion is convex. The lower portion is flat.

Petalage: Under normal conditions, flowers have 40 petals total, about 7 of which are petaloids.

General tonality of flower: Open flowers are Red Group 40A.

Petal color:

*Upon opening, outer petals.*—Upper surface: Red Group 40A. Lower surface: Red Group 52A.

*Upon opening, inner petals.*—Upper surface: Red Group 40A. Lower surface: Red Group 52A.

*Basal petal spots, upon opening.*—Upper surface: Yellow Group 5C. Lower surface: Yellow Group 2D.

*After opening, outer petals.*—Upper surface: Red Group 40A. Lower surface: Red Group 52A.

*After opening, inner petals.*—Upper surface: Red Group 40A. Lower surface: Red Group 52A.

*Basal petal spots, after opening.*—Upper surface: Yellow Group 5C. Lower surface: Yellow Group 2D.

Petals:

*Petal reflex.*—Slightly reflexed.

*Margin.*—Entire and uniform.

*Shape.*—Generally elliptical. Apex shape: Rounded. Base shape: Broadly acute.

*Size.*—30 mm (l)×40 mm (w).

*Texture.*—Smooth.

*Thickness.*—Average.

Petaloids:

*Size.*—12 mm (l) by 6 mm (w).

*Quantity.*—Average 7.

*Shape.*—Elliptical, base and apex are acute.

*Color.*—Red Group 40A on the upper side, and Red Group 52A on the lower side. The base of the petaloid is Yellow Group 5C on the upper surface. Yellow Group 2D on the lower surface.

Reproductive flower parts:

*Pollen.*—None observed.

*Anthers.*—Size: 2 mm in length. Color: Yellow-Orange Group 19A. Quantity: 35 on average.

*Filaments.*—Color: Yellow Group 13C. Length: 4 mm.

*Pistils.*—Length: 8 mm. Quantity: 30 on average.

*Stigmas.*—Color: Yellow-White Group 158B.

*Styles.*—Color: Red Group 56C.

*Location of stigmas.*—Superior in location relative to the length of the filaments and the height of the anthers.

*Hips.*—None observed to date.

PLANT

Plant growth: Upright, bushy. Plants are 50 cm in height, and 50 cm wide.

Stems:

*Color.*—Juvenile growth: Yellow-Green Group 144B. Mature growth: Yellow-Green Group 144A.

*Length.*—On average, canes are 30 cm from the base of the plant to the flowering portion.

*Diameter.*—8 mm.

*Internodes.*—On mature canes about 50 mm between nodes.

*Surface texture.*—Young wood: Small prickles. Older wood: Smooth.

Long prickles:

*Incidence.*—6 prickles per 10 cm of stem.

*Size.*—Average length of prickles on mature stems is 7 mm.

*Shape.*—Upper portion is linear. Lower portion is concave.

*Color.*—Juvenile prickles: Greyed-Orange Group 173C. Mature prickles: Yellow-Green Group 152C.

Plant foliage:

*Compound leaf.*—170 mm (l)×110 (w).

*Quantity.*—2 leaves per 10 cm of stem on average.

*Color of juvenile foliage*.—Upper side: Yellow-Green Group 152A with intonations of Greyed-Red Group 178A. Lower side: Yellow-Green Group 152C with intonations of Greyed-Red Group 178A.

*Color of mature foliage*.—Upper side: Yellow-Green Group 147A. Lower side: Yellow-Green Group 147B.

Plant leaves and leaflets:

*Stipules*.—Size: 23 mm long, 7 mm wide. Quantity: 2 per compound leaf. Shape: Linear, slightly broad based with outward extending apices. Margins: Finely serrated. Color: Yellow-Green Group 144A.

*Petiole*.—Length: About 22 mm. Diameter: 1.5 mm.

*Upper surface*.—Color: Yellow-Green Group 144A.

*Lower surface*.—Color: Yellow-Green Group 144A.

*Rachis*.—Length: About 75 mm. Upper surface: Color: Yellow-Green Group 144A.

*Lower surface*.—Color: Yellow-Green Group 144A. Observations: Small prickles.

*Leaflet*.—Quantity: Normally 5 to 7 leaflets. Margins: Serrated. Size: On average terminal leaflets are 60 mm long, 50 mm wide. Shape: Generally elliptical. Base: Rounded. Apex: Mucronate. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Compact Floribunda rose class named 'Poulcas049', substantially as illustrated and described herein, due to its abundant orange red flowers, disease resistance, and extended period of bloom.

* * * * *